United States Patent [19]
Möller et al.

[11] Patent Number: 5,869,101
[45] Date of Patent: Feb. 9, 1999

[54] PROCESS FOR THE PREPARATION OF S(+)-IBUPROFEN-PARTICLES

[75] Inventors: Torsten Möller, Altenmarkt-Alz, Germany; Gerhard Hantich, Kitzbübel; Ernst Hesse, Fieberbrunn, both of Austria

[73] Assignee: Gebro Borschek Gesellschaft M.B.H., Bahnhofbichl, Austria

[21] Appl. No.: 682,515

[22] PCT Filed: Jan. 26, 1995

[86] PCT No.: PCT/AT95/00014

§ 371 Date: Jul. 12, 1996

§ 102(e) Date: Jul. 12, 1996

[87] PCT Pub. No.: WO95/20382

PCT Pub. Date: Aug. 3, 1995

[30] Foreign Application Priority Data

Jan. 28, 1994 [AT] Austria ...................................... 158/94

[51] Int. Cl.⁶ ...................................................... A61K 9/14
[52] U.S. Cl. .......................... 424/489; 424/494; 424/480; 424/488
[58] Field of Search ..................... 424/489, 465, 424/470; 514/568; 560/60

[56] References Cited

U.S. PATENT DOCUMENTS

| 4,086,346 | 4/1978 | Bocker et al. ........................... 424/253 |
| 4,609,675 | 9/1986 | Franz ....................................... 514/568 |
| 5,191,114 | 3/1993 | Chen ........................................ 562/496 |
| 5,198,568 | 3/1993 | Zepp et al. ................................ 560/60 |

FOREIGN PATENT DOCUMENTS

| 0120587 | 10/1984 | European Pat. Off. . |
| 0299668 | 1/1989 | European Pat. Off. . |
| 0362728 | 4/1990 | European Pat. Off. . |
| 0362731 | 4/1990 | European Pat. Off. . |
| WO 90/03782 | 4/1990 | WIPO . |
| WO 92/08686 | 5/1992 | WIPO . |

OTHER PUBLICATIONS

Database WPI, Week 7744, Derwent Publications Ltd., London, GB; AN 77–78258Y (44) & JP,A,52 111 533, Sep. 19, 1977.

Primary Examiner—Thurman K. Page
Assistant Examiner—William E. Benston, Jr.
Attorney, Agent, or Firm—Jacobson, Price, Holman & Stern, PLLC

[57] ABSTRACT

A process for the production of S(+)-ibuprofen-particles having improved flow properties comprises the steps that coarse-crystalline S(+)-ibuprofen is molten and then in a molten condition is finely distributed in a non-solving medium, preferably in cold water, and is chilled therein. This chilling results in a fine-crystalline primary structure that agglomerates to a secondary structure. In this agglomerate form the product is obtained which is filtered out and is dried. Such particles are suitable for direct pressing of tablets, optionally, tableting auxiliary substances being added, also for the production of tablets having a retarded release of the active substance.

27 Claims, 4 Drawing Sheets

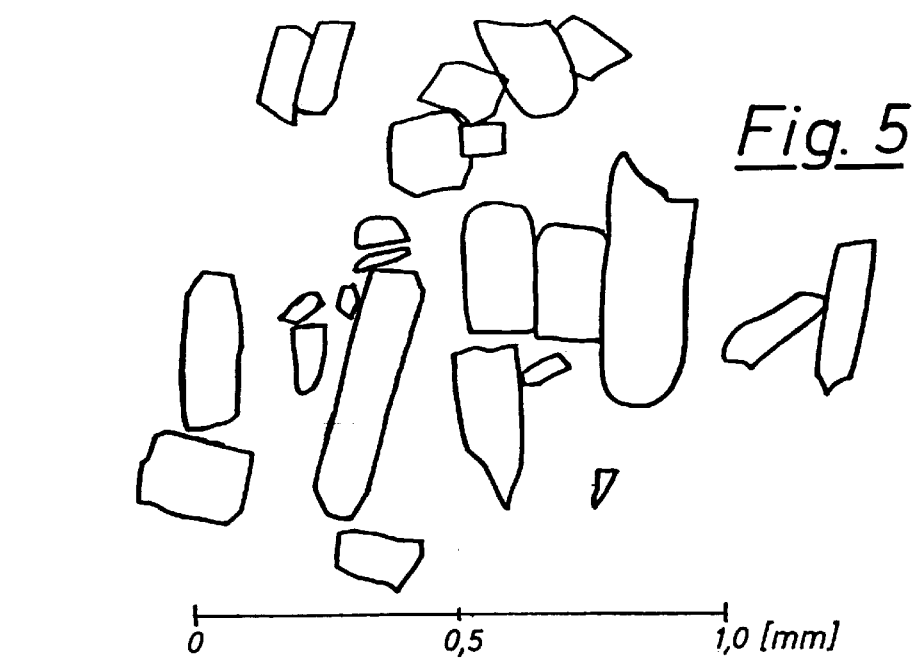
Fig. 5
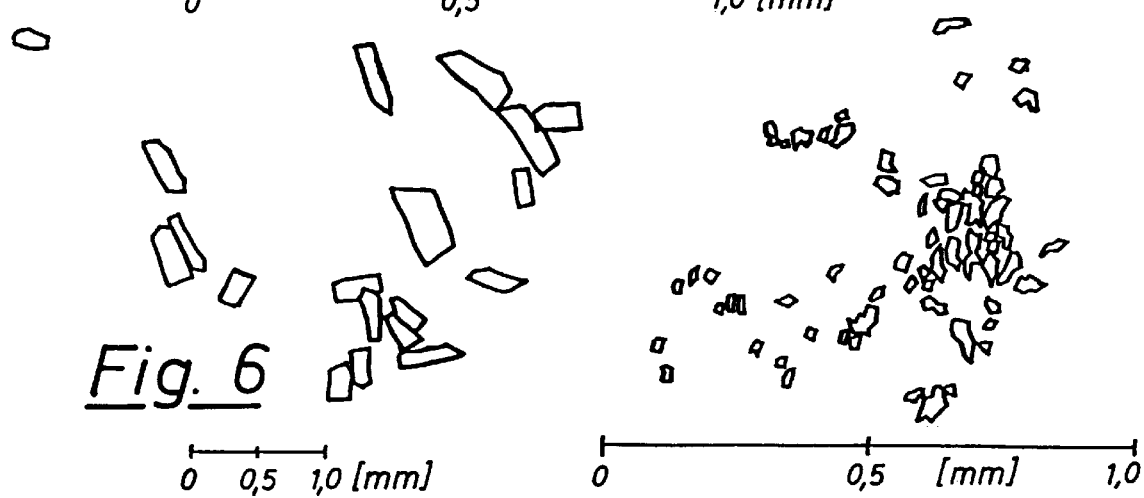
Fig. 6
Fig. 7
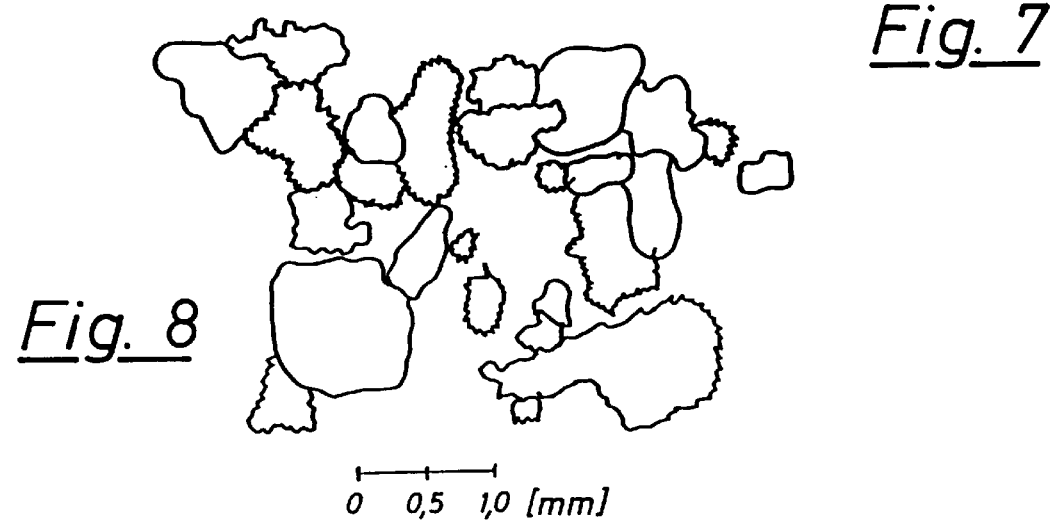
Fig. 8

PROCESS FOR THE PREPARATION OF S(+)-IBUPROFEN-PARTICLES

This application is a 371 of PCT/AT95/00014 filed Jan. 26, 1995.

The invention relates to a process for the preparation of S(+)-ibuprofen-particles having improved flow properties, in particular suitable for filling capsules or for pressing tablets.

As it is well known, the particle size and the crystalline form are decisive parameters for the pharmaceutic-technologic properties of racemic or, respectively, optically pure ibuprofen. It is also known that ibuprofen obtained by different reaction processes shows crystals having the shape of a needle so that they have very poor flow properties or pourability. By these reasons, difficulties occur in connection with galenically processing, for example when pressing tablets or producing capsules. There have been attempts to overcome these difficulties by processing racemic ibuprofen by a crystallisation step (EP-A 120,587, WO 90/03782, WO 92/08686), or by processing it by melting (EP-A 362,728). The first-named kind of processing requires the use of organic solvents what frequently causes problems by environmental reasons. This disadvantage is indeed avoided by the second-named kind of processing, however, the process described there requires considerable effort in apparatus, because the racemic mixture is molten and then cooled on a contact surface. Thereby, scaly-shaped structures are obtained that must be comminutated considering special grinding conditions. For this an effort in apparatus is necessary that is too great in order to allow an economical process.

Further, S(+)-ibuprofen, the pharaceutic activity thereof considerably exceeds that of the racemic mixture, has not only a melting point (50°–54° C.) that is substantially lower than that of the racemic mixture (75°–78° C.), but also shows completely different physical properties, for example a different solvent power inconventional solvents, so that also by these reasons S(+)-ibuprofen cannot be processed along the above described processes.

The invention has at its object to provide a process for the production of S(+)-ibuprofen-particles having improved flow properties, in particular for filling in capsules or for pressing tablets, which process operates economically and, therefore, can be economically carried out in a large scale and without substantial use of organic solvents and therefore without environmental impact, requires less effort in apparatus and also enables a continuous processing. The invention solves this task by the features that granular crystalline S(+)-ibuprofen is molten and then in molten condition is finely distributed in a non-solvent medium, preferably in cold water, and is rapidly chilled for obtaining a fine-grained crystalline primary structure, whereupon the product obtained in agglomerates as a secondary structure is filtered out and dried. The sudden fall of temperature caused by the action of the non-solvent medium on the molten S(+)-ibuprofen, causes that the molten active substance solidifies and crystallizes in a particle shape that in a surprising manner is considerably similar to the shape of granules. Within this, it is over all surprising that a primary structure in form of irregularly shaped crystallites is obtained, which have a ratio of length to width of not more of about 1:2. These crystallites agglomerate to a secondary structure in form of granules having generally a diameter of less than 1 mm and being substantially spheroid and, therefore, have a good pourability. Such particles can be directly pressed in tablets using conventional additives, or, respectively, an exact apportioning can take place for the production of tablets, capsules or other galenic forms. As a rule, it is no more necessary to comminute the obtained granules, only if it is desired to obtain particles of substantially uniform size, a sizing step may be used if necessary, or example, by screening.

FIGS. 5, 7, 9 and 11 show the primary structure of S(+)-ibuprofen prepared according to the invention.

FIGS. 6, 8, 10 and 12 show the secondary structure of S(+)-ibuprofen according to the invention.

Figure 1:
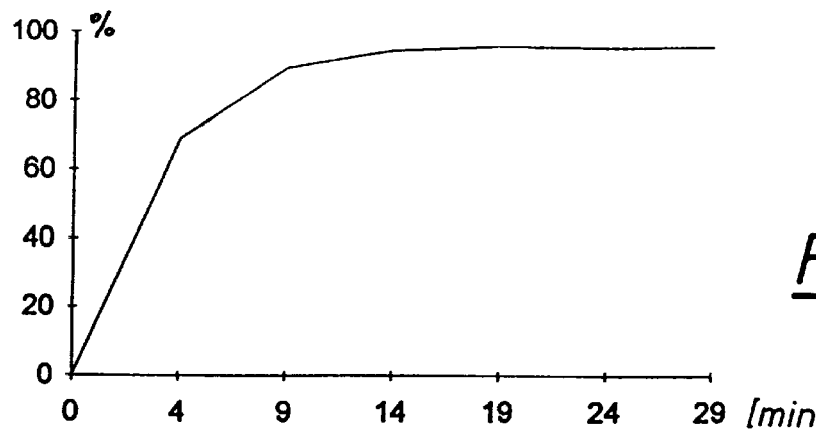
FIGS. 1 and 2 represent a graph of the release rate of a tablet prepared according to the invention.

The inventive process can be carried out without the use of organic solvents and, therefore, avoids any environmental problems. It has a high yield that may amount to more than 99% and, in comparison to processes using organic solvents, has a higher output. The effort in apparatus and time is substantially reduced in comparison to all processes mentioned above. Further, there is the possibility to influence the particle size of the product obtained by variation of the process parameters, what is described more in detail later on. The inventive process can be carried out in batch quantities as well as continuously and can be carried out immediately after the conventional production of optically pure S(+)-ibuprofen from the racemic mixture or, respectively, after the conventional final purification step by crystallisation from hexane. As a rule, commercial S(+)-ibuprofen has at least a content of 98%, minor contents of the R(−)-ibuprofen do not detrimentally influence the inventive process. The advantages of the inventive process and of the product obtained by this process are the more evident the cleaner is the starting material.

Further, it is of advantage within the inventive process, that the obtained product enables one to reduce the quantities of the additives for the galenic further processing, what has as a consequence that the galenic possibilities are increased.

It has not yet been completely investigated why by the inventive process granulate-similar particles are obtained, the ratio of length to width of the particles composed of crystallites does not substantially differ from 1:1. It can be assumed, however, that the high shearing action exerted onto the non-solvent-agent is a substantial factor, because the amount of the shearing action decisively determines the particles size and, therefore, the dissolution velocity of the S(+)-ibuprofen-agglomerate obtained, so that via the amount of the shearing action an adaption to the respective required parameters is possible, as well as an agitation of the non-solving-agent for a quicker distribution of the added molten S(+)-ibuprofen. Preferably, therefore, the inventive process is carried out so that the molten S(+)-ibuprofen is added to the non-solving-medium under an intensive stirring action. As already mentioned, the intensive stirring action as well as the amount of the shearing action decisively influence the particle size of the S(+)-ibuprofen obtained. It is favourable, to use high-speed apparatus for the stirring action (for example the use of an ultra-turrax or a turbo-stirring apparatus), since in such a manner small particle sizes of the agglomerate can be obtained and a subsequent mechanical comminutation of the obtained product can be saved. Within the spirit of the inventive process, the melting temperature amounts up to 62° C. At this temperature, S(+)-ibuprofen as a so-called bulkware is completely molten.

The final drying step of the crystallized product is carried out at not more than 40° C. in order to avoid that the S(+)-ibuprofen is molten again. Suitably, the drying step is carried out in a rack compartment or under vacuum influence. Vacuum drying is of particular advantage because it easily avoids that the product is molten again.

When evaluating the researches carried out, it has been found that the quantity of the non-solving-medium in percents of weight should suitably amount 3 to 7 times the quantity in percents of weight of the S(+)-ibuprofen brought into action, preferably 5 times this quantity. A substantial increase of the water quantity beyond this preferred value does not improve the product properties. This small amount of the cold non-solvent-agent to be used enables one to deal with bigger batches, when compared with processes which use organic solvents. It is most suitable to use cold water as a non-solving medium, however also other conventional non-solving agents may be used for the chilling step, for example mixtures of water with a portion of a few percents of an organic liquid, as methanol, ethanol and the like, wherein carrying out the process, in particular the temperature of the used non-solving medium and, respectively, or the amount of the active substance used, must be so chosen, that no substantial solution of the active substance occurs, that means that at the conditions of the process the non-solving power of the chilling mixture onto the ibuprofen is retained or is not substantially decreased. The term "non-solving medium" is so to be understood that it is admissible that small amounts of the active substance are solved.

By the use of several additives, for example additives that enhance the decomposition, or of binding agents, the parameters of the galenic process can be influenced. By inspection it has been shown in a surprising manner that by the use of S(+)-ibuprofen prepared in the inventive manner, not only tablets could be directly pressed that showed a quick release, so that no expensive granulation steps were necessary, but also the preparation of oral administering forms having a delayed release of the active substance, for example of retard tablets. It can be assumed that the fine-crystalline shape of the obtained crystallites results in an increased packing density of these particles when they agglomerate to the spheroidic particles of the secondary structure, so that the solubility of the particles of the active substance is decreased by decreasing of the free surface. Thereby, the advantage is obtained that no separate matrix is necessary in order to obtain a retard action of the galenic products. Also thereby, the versability of the galenic possibilities is increased.

Optionally, additives assisting the decomposition, for example cross-linked carboxymethylcellulose, cross-linked polyvinyl pyrrolidone or micro-crystallinic cellulose may be added to the melt of the S(+)-ibuprofen, in order to obtain a quicker dissolution for a quicker release of the active substance. Also, conventional binding agents, for example cellulose derivates, in particular hydroxypropylmethylcellulose, may be used.

In the following, the inventive process is described by way of some examples:

EXAMPLE 1

100,0 g coarse-crystallinic S(+)-ibuprofen are heated in a special steel vessel by means of a heating plate. When 60° C. product temperature is reached, the active substance is completely molten.

500,0 g cold water (room temperature, about 20° C.) are poured into a suitable vessel (beaker glass) and are stirred by means of a magnetic stirring apparatus.

The S(+)-ibuprofen melt is added to the water in one single pouring step, continuing the stirring action. After a short time a solit granulate-shaped product is developed, which subsequently is separated from the aqueous phase by means of a suitable filter means. The final product is dried for 2 hours at 40° C. under vacuum and subsequently is screened by means of a 1.25 mm-Frewift-sieve. (The final temperature of the water after solidification of the melt amounts to 27° C.).

EXAMPLE 2

100,0 g coarse-crystalline S(+)-ibuprofen are crystallized out according example 1 in 500.0 g cold water. Instead of a turbo-stirring apparatus, an ultra-turrax-stirring apparatus is used. The obtained product is dried for 2 hours at 40° C. under vacuum. A final comminution or, respectively, screening according to example 1 is not necessary, since the particle diameter amounts to less than 1.25 mm (final temperature of the water: 27° C.).

EXAMPLE 3

120.0 g coarse-crystalline S(+)-ibuprofen are molten according example 1 and 2 and in the melt 13.0 g calcium-carboxymethylcellulose are dispersed by stirring using a magnetic stirring apparatus. Subsequently, the dispersion is added in one single pouring step to 800 g cold water which is stirred by an ultra-turrax-stirring apparatus. The further operation steps correspond to those of example 2. Also in this example no further comminution and no screening step is necessary due to the small size of the agglomerates. (Final temperature of the water: 23° C.).

EXAMPLE 4

10 kg coarse-crystalline S(+)-ibuprofen are heated in a special steel vessel by means of a heating plate. At 62° C. product temperature, the active substance is completely molten.

50 kg water (about 20° C.) are filled into a 150 l stainless steel vessel and are stirred by means of a turbo stirring apparatus. The molten S(+)-ibuprofen melt is added to the water in one single pouring step, and after 20 seconds a product crystallizes out, which is filtered out and is dried under vacuum at 40° C. for 2 hours.

Subsequently, the final product is screened using a 1.25 mm-Frewitt-sieve. (Final temperature of the water: 26° C.).

EXAMPLE 5

200 g coarse-crystalline S(+)-ibuprofen are heated in a special steel vessel by means of a heating plate. At about 60° C. product temperature, the active substance is completely molten.

1000 g water of about 20° C. are filled into a beaker glass and are stirred by an ultra-turrax.

The S(+)-ibuprofen melt is subsequently continuously added drop by drop, and in the course of which a fine product crystallized out. This product is dried under vacuum at 40° C. for 2 hours. A comminution is not necessary. (Final temperature of the water: 28° C.).

EXAMPLE 6

200 g coarse-crystalline S(+)-ibuprofen are molten according to example 5 and are crystallized out by adding to cold water. The introduction of the melt into the non-solving medium was made by injection by means of a heated nozzle.

The obtained fine product is filtered out and is dried at 40° C. under vacuum. A further comminution is not necessary. (Final temperature of the water: 27° C.).

EXAMPLE 7

300 g coarse-crystalline S(+)-ibuprofen are molten in a beaker glass (at 60° C. product temperature) and are stirred up by means of an ultra-turrax. Then 1.5 kg water (20° C.) are added in one single pouring step; the stirring operation is continued and a fine product is obtained which is filtered out and is dried at 40° C. for 2 hours under vacuum. A further comminution is not necessary. (Final temperature of the water: 27° C.).

Examplative Recipe for a S(+)-Ibuprofen Tablet Containing Active Substance that is Prepared in the Inventive Manner (values in mg/tablet)

For the preparation of the tablet the following components are mixed:

| | |
|---|---|
| S(+)-ibuprofen obtained according to example 4 | 300.0 |
| microcrystalline cellulose | 96.0 |
| calcium-carboxymethylcellulose | 15.0 |
| talcum | 15.0 |

The tablet is prepared from the mixture by direct pressing. The ready tablet has the following measured values:

| | |
|---|---|
| tablet mass | 426 mg |
| breaking strength | 11 kp |
| shape | round, vaulted |
| diameter | 11 mm |
| disintegration time in H$_2$O (37° C.) | max. 1: 45 min |

The release of the active substance from the so obtained tablets has been investigated. The medium was phosphate buffer pH 7.2. The result is shown in form of a diagram in FIG. 1, whereby at the ordinate the released active substance is outlined as % and at the abscissa the time is outlined as minutes.

Examplative Recipe for a Hard Gelatine Capsule Containing Active Substance Prepared in the Inventive Manner (Quantity: 105 g)

The following components were mixed:

| | |
|---|---|
| S(+)-ibuprofen, prepared according to example 1 | 100.0 g |
| talcum | 5.0 g |

The mixture shows excellent flowing properties. The capsules were filled on a conventional laboratory apparatus. 190.5 mg filling mass were used per capsule, that corresponds to 181.5 mg S(+)-ibuprofen.

Figure 2:
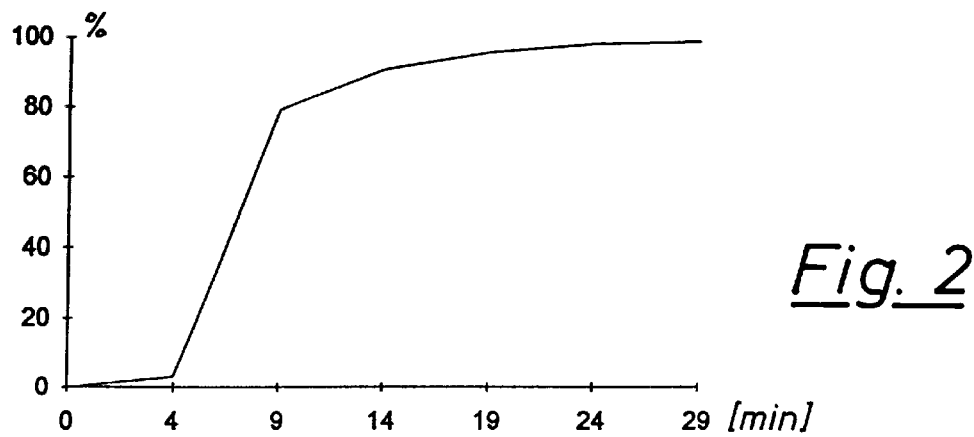

The so prepared capsules were investigated with respect to the release of the active substance. The results are shown in the diagram of FIG. 2, wherein at the ordinate the released active substance is outlined as % and at the abscissa the time is outlined as minutes.

Examplative Recipe for a Retarded S(+)-Ibuprofen Tablet Containing Active Substance Prepared in the Inventive Manner (Quantities in Mg/Tablet)

The following components were mixed:

| | |
|---|---|
| S(+)-ibuprofen obtained according to example 4 | 400.0 |
| hydroxypropylmethylcellulose | 40.0 |
| montanglycolwax | 40.0 |
| microdispersed silicon dioxide | 2.7 |
| talcum | 33.3 |

From the mixture tablets were prepared by direct pressing, having the following properties:

| | |
|---|---|
| tablet mass | 516.0 mg |
| breaking strength | 9 kp |
| shape | round, vaulted |
| diameter | 11 mm |

Figure 3:
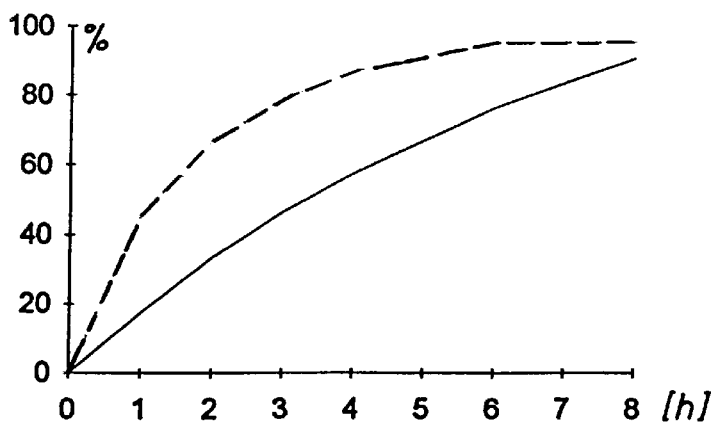
FIG. 3 represents a graph of the release rate of a tablet prepared according to the invention and a tablet containing coarse-crystalline active substance.

The so prepared tablets were investigated with respect to the release of the active substance, using phosphate buffer pH 7.2 as the medium. Under the same conditions, identically prepared tablets were investigated that contained coarse-crystalline active substance prepared in the conventional manner. The results are contained in the diagram according to FIG. 3 in which at the ordinate the released active substance is outlined as % and at the abscissa the time is outlined as hours. The release course for the tablets containing the active substance prepared in the inventive manner is shown by full lines, whereas the comparison tablets containing coarse-crystalline active substance resulted in the release course shown by broken lines. It can be seen that the retard properties of the tablets containing the active substance prepared in the inventive manner were substantially more favourable.

Dissolution Behaviour of S(+)-Ibuprofen

The following mode of procedure was used:

400 mg S(+)-ibuprofen were exactly weighed and were added to 900 ml warmed phosphate buffer (37° C.) of pH 7.2. After 2, 4, 6, 8, 10 and 12 minutes samples were taken and subsequently the dissoluted active substance was determined. The dissolution tests were made by means of a common test apparatus using the Paddle-method (six-fold-determination).

The following results were obtained:

The investigation of the tests gave the result that the inventive prepared S(+)-ibuprofen in the first minutes is solved in the medium somewhat slowlier than coarse-crystalline active substance. After about 10 minutes the coarse-crystalline S(+)-ibuprofen as well as the S(+)-ibuprofen prepared in the inventive manner were completely solved. Probably, the reason for this delayed dissolution behaviour is the aggregation of the crystallites to bigger agglomerates, so that a comparatively less surface of the active substance is contacted by the medium.

Figure 4:
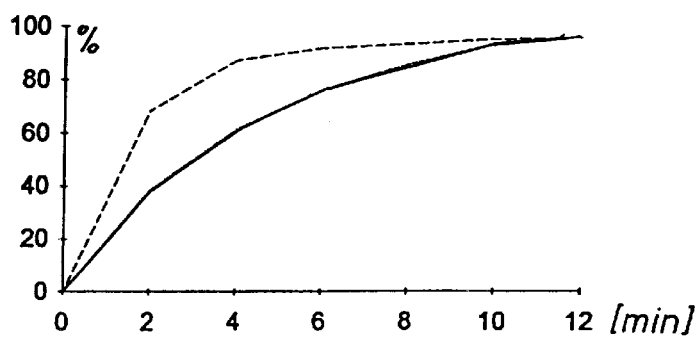
FIG. 4 represents a graph of the dissolution rate of S(+)-ibuprofen prepared according to the invention and prepared by conventional methods.
Figure 9:
Figure 10:
Figure 11:
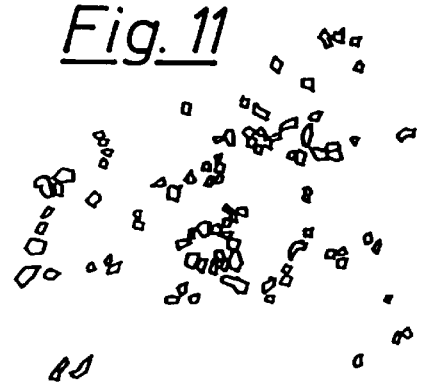
Figure 12:
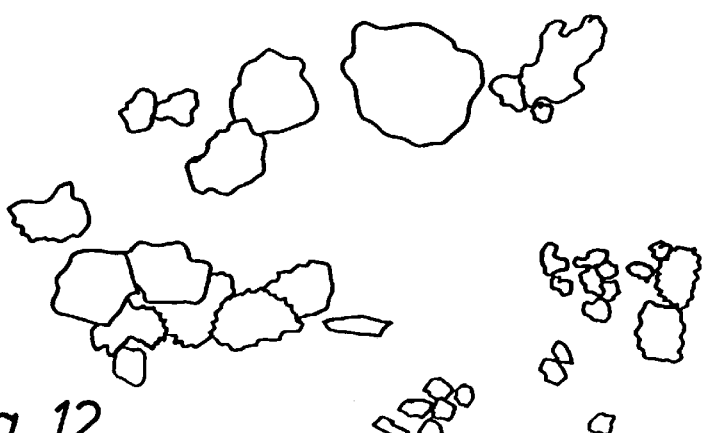

The results are shown in the diagram according to FIG. 4, in which at the ordinate the solved active substance is outlined as % and at the abscissa the time is outlined as minutes. The course shown by full lines corresponds to the S(+)-ibuprofen prepared according to the invention, whereas the course shown by broken lines corresponds to coarse-crystalline, conventionally prepared S(+)-ibuprofen.

Structure Characteristics of S(+)-Ibuprofen

The structures of S(+)-ibuprofen obtained in the inventive manner and of S(+)-ibuprofen prepared in a conventional manner were investigated under the microscope. The results are shown in FIGS. 5 to 12, the FIGS. 5, 7, 9 and 11 each showing the primary structure in about 80-fold magnification, and in FIGS. 6, 8, 10 and 12 the secondary structure is shown in about 20-fold magnification. This was the result:

1. Coarse-crystalline S(+)-ibuprofen prepared in a conventional manner:

The primary structure (FIG. 5) corresponds to the secondary structure (FIG. 6). There were glassy translucent crystals of a column-like shape having a smooth surface. The material contains relatively much fragment material. The length of the single crystals amounts up to 500 μm, the width up to 150 μm, the ratio length:width, as an average, about 1:3.

2. S(+)-ibuprofen prepared in the inventive manner according to example 1 by means of a magnetic stirring apparatus:

As the primary structure (FIG. 7) irregularly shaped spheroid crystallites of relatively uniform size are obtained. The length of these crystallites amounts up to 60 μm, the width up to 30 μm, the ratio length:width, as an average, is 1:1 to 1:2.

As the secondary structure (FIG. 8), crystallite agglomerates having partially smooth surfaces were obtained. To some extent, the single crystallites can be seen. The diameter of the agglomerates varies considerably and amounts to about 1.5 mm.

3. S(+)-ibuprofen prepared in the inventive manner according to example 2 by means of an ultra-turrax:

The primary structure (FIG. 9) shows irregularly shaped spheroid crystallites having a relatively uniform size. The length amounts up to 50 μm, the width up to 20 μm, the ratio length:width, as an average, about 1:1.

As the secondary structure (FIG. 10), a crystallite agglomeration having an intensively structured surface was obtained. The diameter of the agglomerates varies for a relatively small amount, it amounts up to 1.0 mm.

4. S(+)-ibuprofen prepared in the inventive manner according to example 3, using calcium-carboxymethylcellulose as an additive:

As the primary structure (FIG. 11), irregularly shaped spheroidic crystallites having a relatively uniform size were obtained. The length of these crystallites amounts up to 50 μm, the width up to 30 μm, the ratio length:width, as an average, amounts to about 1:1.

As the secondary structure (FIG. 12), an only partially marked crystallite agglomeration having many individual crystallites was obtained. Smooth brilliant surfaces were dominating. The agglomerate diameter amounts up to 1.5 mm.

Identification of S(+)-Ibuprofen Prepared in the Inventive Manner in Solid Medicaments (Tablets, Dragées, Capsules)

The differences of the crystal shape and the crystal size between common coarse-crystalline S(+)-ibuprofen and S(+)-ibuprofen obtained by the inventive process are so important that (in dependency from the additives used) a relatively reliable identification of the process according to which the active substance was obtained, is possible. As a rule, the S(+)-ibuprofen-content is always very high so that only the main component of the medicine must be investigated. For this, the tablet or the dragee or the content of a capsule is carefully pulverized by means of a mortar and a pestle, and the obtained powder is inspected using a microscope.

Figure 13:
FIG. 13 shows a sample containing coarse-crystalline active substance obtained by conventional methods.
Figure 13:
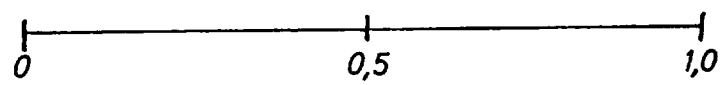
Figure 14:
FIG. 14 shows a sample containing active substance prepared according to the invention.
Figure 14:
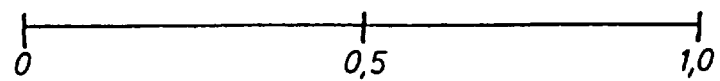

FIGS. 13 and 14 show, respectively, a sample containing coarse-crystalline active substance obtained in a conventional manner (FIG. 13), and a sample containing active substance prepared in the inventive manner (FIG. 14) always using about 90-fold magnification.

We claim:

1. A process for preparing S(+)ibuprofen-particles having improved flow properties, comprising:

obtaining coarse-crystalline S(+)-ibuprofen in a molten form;

finely distributing the molten form of S(+)-ibuprofen in a non-solvent medium; chilling the molten S(+)-ibuprofen in the non-solvent medium so as to obtain a S(+)-ibuprofen product in a fine-crystalline primary structure, wherein the product agglomerates to a secondary structure; and filtering out and drying the agglomerate.

2. The process of claim 1 wherein the S(+)-ibuprofen particles obtained are suitable for filling capsules or pressing into tablet form.

3. The process of claim 1 wherein the non-solvent medium is cold water.

4. The process of claim 1 wherein the molten form of S(+)-ibuprofen is added to the non-solvent medium under intensive stirring action.

5. The process of claim 4 wherein high-speed tools are used for the stirring action.

6. The process of claim 1 wherein the molten form of S(+)-ibuprofen is added to the non-solvent medium in one single pouring step.

7. The process of claim 1 wherein the molten form of S(+)-ibuprofen is injected into the non-solvent medium through a heated nozzle.

8. The process of claim 1 wherein the molten form of S(+)-ibuprofen is obtained by heating up to a temperature of about 62° C.

9. The process of claim 1 wherein drying occurs at a maximum temperature of about 40° C.

10. The process of claim 9 wherein drying occurs under vacuum or in a rack compartment.

11. The process of claim 1 wherein the amount of non-solvent medium, in percent by weight, is 3 to 7 times that of the amount of S(+)-ibuprofen.

12. The process of claim 11 wherein the amount of non-solvent medium, in percent by weight, is 5 times that of the amount of S(+)-ibuprofen.

13. The process of claim 1 wherein the non-solvent medium is water and at least one organic liquid and in carrying out the process no substantial solution of the active substance occurs.

14. The process of claim 1 wherein the non-solvent medium is water and at least one organic liquid.

15. The process of claim 14 wherein the at least one organic liquid is selected from the group consisting of methanol and ethanol.

16. The process of claim 1 wherein substances enhancing disintegration or binders are added to the molten S(+)-ibuprofen.

17. The process of claim 16 wherein the substances enhancing disintegration are selected from the group consisting of cross-linked carboxymethylcellulose, cross-linked polyvinylpyrrolidone and micro-crystalline cellulose.

18. The process of claim 16 wherein the binders are selected from the group consisting of cellulose derivatives.

19. The process of claim 18 wherein the cellulose derivative is hydroxypropylmethylcellulose.

20. S(+)-ibuprofen-particles in the form of crystallites having a fine crystalline primary structure and agglomerating to a secondary structure.

21. S(+)-ibuprofen-particles obtained by a process of claim 1.

22. The S(+)-ibuprofen-particles according to claim 21 in medicinal forms suitable for administration, forms being selected from the group consisting of directly pressed tablets and gelatine capsules.

23. The S(+)-ibuprofen-particles according to claim 22 in tablet form.

24. The S(+)-ibuprofen-particles according to claim 23 wherein the tablets are slow release tablets.

25. The S(+)-ibuprofen-particles according to claim 22 in gelatine capsule form.

26. The S(+)-ibuprofen-particles according to claim 22 further comprising auxiliary substances and/or carrier substances.

27. The S(+)-ibuprofen-particles according to claim 22 wherein when in a tablet form, so as to produce a slow release tablet, auxiliary substances are added during preparation of the tablets.

* * * * *